US011116585B2

(12) United States Patent
Lyons et al.

(10) Patent No.: US 11,116,585 B2
(45) Date of Patent: Sep. 14, 2021

(54) GRAPHICAL USER INTERFACES FOR ABLATION SYSTEMS

(71) Applicant: Apama Medical, Inc., Campbell, CA (US)

(72) Inventors: Gerald Lyons, Saratoga, CA (US); Daniel Lundberg, Campbell, CA (US); Ronald Avisa, Newark, CA (US); Rodica Schileru, San Jose, CA (US); Adnan Merchant, Fremont, CA (US); Jeffrey N. Gamelsky, Palo Alto, CA (US)

(73) Assignee: Apama Medical, Inc., Campbell, CA (US)

( * ) Notice: Subject to any disclaimer, the term of this patent is extended or adjusted under 35 U.S.C. 154(b) by 471 days.

(21) Appl. No.: 16/013,689

(22) Filed: Jun. 20, 2018

(65) Prior Publication Data

US 2018/0368927 A1   Dec. 27, 2018

Related U.S. Application Data

(60) Provisional application No. 62/523,198, filed on Jun. 21, 2017.

(51) Int. Cl.
*A61B 18/12* (2006.01)
*A61B 34/00* (2016.01)
(Continued)

(52) U.S. Cl.
CPC .......... *A61B 34/25* (2016.02); *A61B 1/00006* (2013.01); *A61B 1/00039* (2013.01);
(Continued)

(58) Field of Classification Search
CPC ............ A61B 18/1206; A61B 18/1492; A61B 1/00006; A61B 1/00039; A61B 1/00045; A61B 1/05; A61B 1/0676; A61B 2017/00026; A61B 2017/00199; A61B 2017/00243; A61B 2017/00296; A61B 2018/00011; A61B 2018/0016; A61B 2018/00214; A61B 2018/0022;
(Continued)

(56) References Cited

U.S. PATENT DOCUMENTS

| 949,226 A | 2/1910 | Goodman |
| 6,258,087 B1 | 7/2001 | Edwards et al. |

(Continued)

FOREIGN PATENT DOCUMENTS

WO   WO2017184628 A1   10/2017

OTHER PUBLICATIONS

International Search Report and Written Opinion issued in PCT/US2018/038589, dated Oct. 8, 2018, 10 pages.

*Primary Examiner* — Michael F Peffley
*Assistant Examiner* — Amanda L Zink
(74) *Attorney, Agent, or Firm* — Faegre Drinker Biddle & Reath LLP

(57) ABSTRACT

A computer-implemented method for generating and displaying a graphical user interface (GUI) is disclosed. The method includes displaying, via the GUI, a real-time video received from a camera disposed within an ablation catheter. The method further includes displaying, via the GUI, a graphical representation of a plurality of electrodes of the ablation catheter.

9 Claims, 14 Drawing Sheets

(51) Int. Cl.
  *A61B 18/14* (2006.01)
  *A61B 1/00* (2006.01)
  *A61B 1/05* (2006.01)
  *A61B 1/06* (2006.01)
  *G16H 40/63* (2018.01)
  *A61B 90/00* (2016.01)
  *A61B 17/00* (2006.01)
  *A61B 18/00* (2006.01)
  *G06F 3/0484* (2013.01)
  *A61B 90/30* (2016.01)

(52) U.S. Cl.
  CPC ............ *A61B 1/00045* (2013.01); *A61B 1/05* (2013.01); *A61B 1/0676* (2013.01); *A61B 18/1206* (2013.01); *A61B 18/1492* (2013.01); *A61B 90/37* (2016.02); *G16H 40/63* (2018.01); *A61B 90/361* (2016.02); *A61B 2017/00026* (2013.01); *A61B 2017/00199* (2013.01); *A61B 2017/00243* (2013.01); *A61B 2017/00296* (2013.01); *A61B 2018/00011* (2013.01); *A61B 2018/0016* (2013.01); *A61B 2018/0022* (2013.01); *A61B 2018/00214* (2013.01); *A61B 2018/00357* (2013.01); *A61B 2018/00577* (2013.01); *A61B 2018/00654* (2013.01); *A61B 2018/00702* (2013.01); *A61B 2018/00875* (2013.01); *A61B 2018/00982* (2013.01); *A61B 2018/1467* (2013.01); *A61B 2034/252* (2016.02); *A61B 2090/309* (2016.02); *A61B 2090/371* (2016.02); *A61B 2218/002* (2013.01); *G06F 3/04847* (2013.01)

(58) Field of Classification Search
  CPC ........... A61B 2018/00357; A61B 2018/00577; A61B 2018/00654; A61B 2018/00702; A61B 2018/00875; A61B 2018/00982; A61B 2018/1467; A61B 2034/252; A61B 2090/309; A61B 2090/371; A61B 2218/002; A61B 34/25; A61B 90/361; A61B 90/37; G06F 3/04847; G16H 40/63
  See application file for complete search history.

(56) References Cited

U.S. PATENT DOCUMENTS

| | | | |
|---|---|---|---|
| 6,451,015 B1* | 9/2002 | Rittman, III | A61B 18/1206 600/523 |
| 9,333,031 B2 | 5/2016 | Salahieh et al. | |
| D815,131 S | 4/2018 | Thompson et al. | |
| 2001/0044585 A1 | 11/2001 | Dupree et al. | |
| 2002/0068931 A1* | 6/2002 | Wong | A61B 18/1206 606/34 |
| 2003/0130711 A1* | 7/2003 | Pearson | A61B 18/1477 607/101 |
| 2005/0203375 A1* | 9/2005 | Willis | A61B 8/445 600/407 |
| 2006/0095022 A1* | 5/2006 | Moll | A61B 46/10 606/1 |
| 2008/0058794 A1 | 3/2008 | MacAdam et al. | |
| 2008/0262489 A1 | 10/2008 | Steinke | |
| 2012/0245575 A1 | 9/2012 | Epstein et al. | |
| 2014/0171942 A1 | 6/2014 | Werneth et al. | |
| 2015/0169836 A1 | 6/2015 | Vahala et al. | |
| 2016/0000500 A1* | 1/2016 | Salahieh | A61B 1/313 600/104 |
| 2017/0333125 A1 | 11/2017 | Lepak et al. | |

* cited by examiner

GRAPHICAL USER INTERFACES FOR ABLATION SYSTEMS

CROSS-REFERENCE TO RELATED APPLICATION

This application claims priority to Provisional Application No. 62/523,198, filed Jun. 21, 2017, which is herein incorporated by reference in its entirety.

TECHNICAL FIELD

The present disclosure relates generally to visualization systems, devices, and methods involving cardiac ablation.

BACKGROUND

Cardiac ablation is a procedure by which cardiac tissue is treated to inactivate the tissue. The tissue targeted for ablation may be associated with improper electrical activity, for example. Cardiac ablation can create lesions in the tissue and prevent the tissue from improperly generating or conducting electrical signals.

SUMMARY

In Example 1, a computer-implemented method for generating and displaying a graphical user interface (GUI) is disclosed. The method includes displaying, via the GUI, a real-time video received from a camera disposed within an ablation catheter. The method further includes displaying, via the GUI, a graphical representation of a plurality of electrodes of the ablation catheter.

In Example 2, the method of Example 1, wherein the GUI displays the real-time video in a first circular region, and wherein the GUI displays the graphical representation in a second circular region.

In Example 3, the method of Example 2, wherein the first circular region and the second circular region are positioned adjacent to each other on the GUI.

In Example 4, the method of any of Examples 1-3, wherein the displaying the real-time video includes displaying video received from a plurality of cameras disposed within the ablation catheter.

In Example 5, the method of any of Examples 1-4, wherein the graphical representation includes an electrode icon for each of the plurality of electrodes of the ablation catheter.

In Example 6, the method of Example 5, further comprising displaying real-time electrical impedance within selected electrode icons.

In Example 7, the method of Example 6, wherein the displayed real-time electrical impedance is based on electrical impedance sensed by the ablation electrodes.

In Example 8, the method of any of Example 5-7, further comprising displaying, via the GUI, highlighted electrode icons; and assigning each highlighted electrode icon as being a source electrode or a sink electrode.

In Example 9, the method of Example 8, wherein only the electrode icons associated with a source electrode display electrical impedance.

In Example 10, the method of any of Example 1-9, further comprising displaying, via the GUI, respective icons for controlling irrigation fluid flow rate, illumination power, and ablation electrode power.

In Example 11, the method of any of Example 1-10, wherein the graphical representation includes an electrode icon corresponding to each of the electrodes of the ablation catheter.

In Example 12, the method of any of Examples 1-11, further comprising displaying icons associated with functions of the real-time video adjacent the real-time video; displaying icons associated with functions of the graphical representation adjacent the real-time graphical representation; and displaying icons associated with an ablation procedure within a ribbon.

In Example 13, a computing device adapted to execute the steps of the method of Examples 1-12.

In Example 14, a computer program product comprising instructions to cause one or more processors to carry out the steps of the method of Examples 1-12.

In Example 15, a computer-readable medium having stored thereon the computer program product of Example 14.

In Example 16, an ablation system includes a radiofrequency (RF) generator configured to generate RF energy and one or more controllers in communication with the RF generator. The one or more controllers are configured to generate a real-time video from an ablation catheter for displaying via a graphical user interface (GUI), and generate a graphical representation including electrode icons corresponding to a plurality of electrodes of the ablation catheter for displaying via the GUI, receive input, via the graphical representation, selecting at least some of the electrode icons, and cause the RF generator to transmit RF energy to the plurality of electrodes of the ablation catheter corresponding to the selected electrode icons.

In Example 17, the ablation system of Example 16, further comprising the ablation catheter in communication with the RF generator and including an expandable member carrying the plurality of electrodes.

In Example 18, the ablation system of Example 17, wherein the ablation catheter includes cameras for generating video for the real-time video of the GUI.

In Example 19, the ablation system of Example 17, wherein the plurality of electrodes are configured to sense electrical impedance.

In Example 20, the ablation system of Example 19, wherein the one or more controllers is configured to generate electrical impedance plots to be displayed within at least some of the electrode icons on the GUI, the electrical impedance plots based on the sensed electrical impedance.

In Example 21, the ablation system of Example 17, wherein the ablation catheter includes an illumination source, wherein the GUI includes an illumination icon for selecting power to the illumination source, wherein the one or more controllers is configured to modify power to the illumination source based on the selected power from the illumination icon.

In Example 22, the ablation system of Example 16, further comprising a display in communication with the one or more controllers and configured to display the GUI.

In Example 23, the ablation system of Example 16, further comprising a computer readable storage medium having program code stored thereon for execution by the one or more controllers to generate the GUI.

In Example 24, the ablation system of Example 16, wherein the one or more controllers is configured to generate electrical impedance plots to be displayed within at least some of the electrode icons in the GUI.

In Example 25, the ablation system of Example 16, wherein the electrode icons of the graphical representation are selectable via the GUI, wherein the one or more controllers is configured to assign the selected electrode icons as either a source electrode or a sink electrode.

In Example 26, the ablation system of Example 16, wherein the RF generator and the one or more controllers are housed in a single console.

In Example 27, a computing device for generating a graphical user interface (GUI) is disclosed. The computing device includes one or more controllers configured to generate a real-time video from an ablation catheter for displaying via the GUI, and generate a graphical representation including electrode icons corresponding to a plurality of electrodes of the ablation catheter for displaying via the GUI.

In Example 28, the computing device of Example 27, wherein the real-time video is to be displayed in a first circular region of the GUI, and wherein the graphical representation is to be displayed in a second circular region.

In Example 29, the computing device of Example 28, wherein the first circular region and the second circular region are positioned adjacent to each other on the GUI.

In Example 30, the computing device of Example 27, wherein the graphical representation includes an electrode icon for each of the plurality of electrodes of the ablation catheter.

In Example 31, the computing device of Example 30, wherein the one or more controllers is configured to generate real-time electrical impedance plots for displaying within at least some of the electrode icons.

In Example 32, the computing device of Example 27, wherein the electrode icons are selectable via the GUI, wherein the one or more controllers is configured to assign selected electrode icons as being a source electrode or a sink electrode.

In Example 33, the computing device of Example 27, wherein the one or more controllers is configured to generate, for display on the GUI, respective icons for controlling irrigation fluid flow rate, illumination power, and ablation electrode power.

In Example 34, the computing device of Example 27, wherein the electrode icons are selectable via the GUI, wherein the one or more controllers is configured to initiate radiofrequency energy transmission to ablation electrodes associated with the selected electrode icons.

In Example 35, the computing device of Example 27, wherein the one or more controllers is configured to generate, for display in the GUI adjacent the real-time video, icons associated with functions of the real-time video; and generate, for display in the GUI adjacent the real-time graphical representation, icons associated with functions of the graphical representation.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
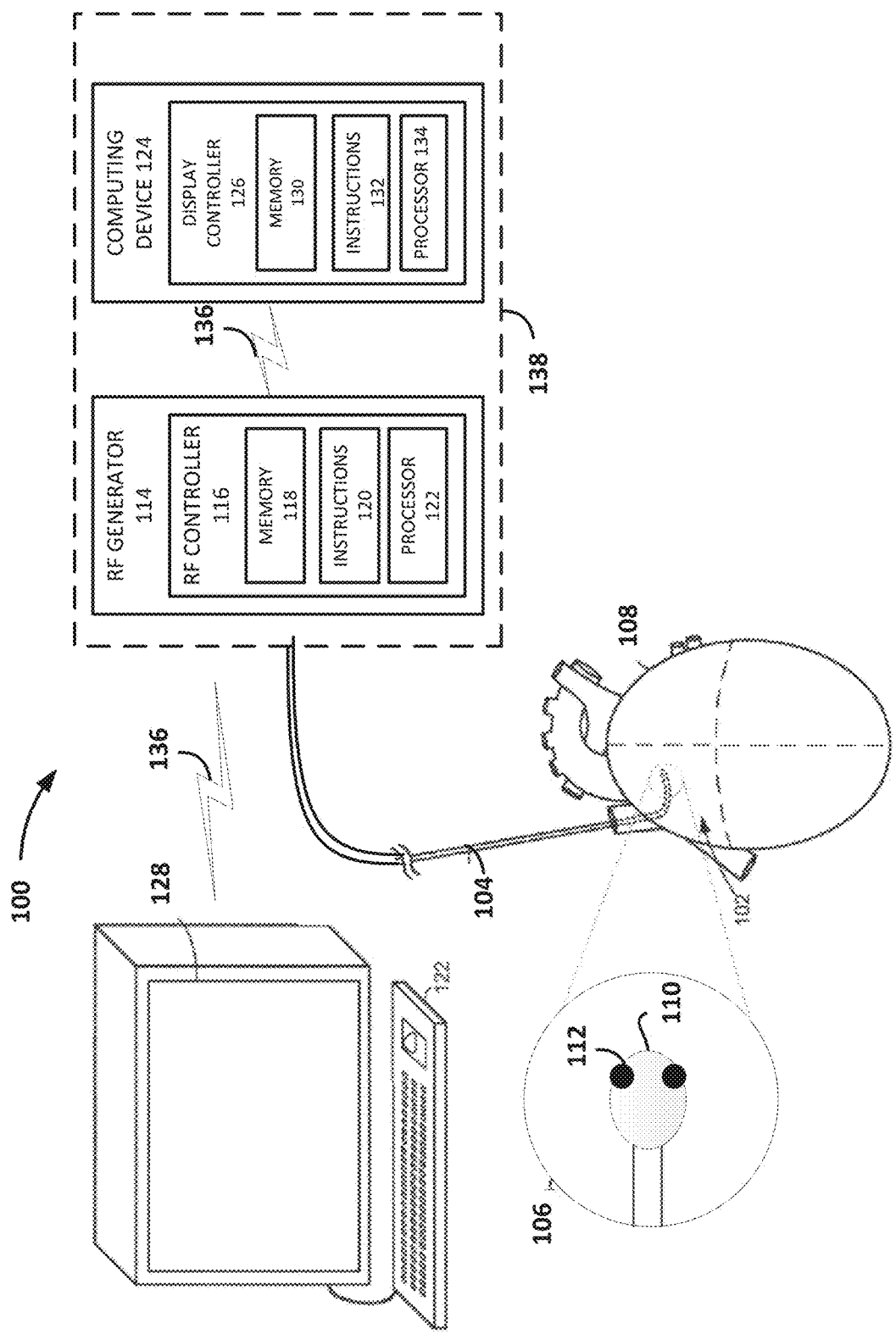
FIG. 1 shows an ablation system, in accordance with certain embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various cardiac abnormalities can be attributed to improper electrical activity of cardiac tissue. Such improper electrical activity can include, but is not limited to, generation of electrical signals, conduction of electrical signals of the tissue, etc., in a manner that does not support efficient and/or effective cardiac function. For example, an area of cardiac tissue may become electrically active prematurely or otherwise out of synchrony during the cardiac cycle, causing the cardiac cells of the area and/or adjacent areas to contract out of rhythm. The result is an abnormal cardiac contraction that is not timed for optimal cardiac output. In some cases, an area of cardiac tissue may provide a faulty electrical pathway (e.g., a short circuit) that causes an arrhythmia, such as atrial fibrillation or supraventricular tachycardia. In some cases, inactive tissue (e.g., scar tissue) may be preferable to malfunctioning cardiac tissue.

Cardiac ablation is a procedure by which cardiac tissue is treated to inactivate the tissue. The tissue targeted for ablation may be associated with improper electrical activity, as described above. Cardiac ablation can create lesions in the tissue and prevent the tissue from improperly generating or conducting electrical signals. For example, a line, a circle, or other formation of ablated cardiac tissue can block the propagation of errant electrical signals. In some cases, cardiac ablation is intended to cause the death of cardiac tissue and to have scar tissue reform over the lesion, where the scar tissue is not associated with the improper electrical activity.

Certain embodiments of the present disclosure involve visualization systems, devices, and methods that can be used in connection with cardiac ablation. In particular, the present disclosure describes graphical user interfaces that display real-time video from an ablation catheter along with a graphical representation of features of the ablation catheter. The graphical representation can be used for, among other things, making real-time modifications to ablation parameters (e.g., modifying power to one or more ablation electrodes, modifying illumination, modifying cooling fluid flow rates), viewing ablation parameters, and monitoring lesion formation. Displaying both the real-time video and graphical representation gives physicians, etc., a level of control, customization, and monitoring not provided by other ablation systems.

FIG. 1 shows an ablation system 100 including an ablation catheter 102 comprising an elongated catheter body 104 and a distal catheter region 106, which is configured to be positioned within a heart 108. The ablation catheter 102 includes an expandable member 110 (e.g., membrane, balloon) and a plurality of energy delivery elements 112 (e.g., ablation electrodes) secured to the expandable member 110.

The energy delivery elements 112 are configured and positioned to deliver ablative energy (e.g., radiofrequency energy) to tissue when the expandable member 110 is inflated.

The system 100 includes a radiofrequency (RF) generator 114 electrically coupled to the plurality of energy delivery elements 112 and configured to generate RF energy. The RF generator 114 includes an RF generator controller 116 configured to control the RF energy to the plurality of energy delivery elements 112. The RF generator controller 116 can be implemented using firmware, integrated circuits, and/or software modules that interact with each other or are combined together. For example, the RF generator controller 116 may include memory 118 storing computer-readable instructions/code 120 for execution by a processor 122 (e.g., microprocessor) to perform aspects of embodiments of methods and procedures discussed herein.

The system 100 can also include a computing device 124 (e.g., personal computer) with a display controller 126 configured to communicate with various components of the system 100 and generate a graphical user interface (GUI) to be displayed via a display 128 (e.g., computer monitor, television, mobile device screen). The display controller 126 can be implemented using firmware, integrated circuits, and/or software modules that interact with each other or are combined together. For example, the display controller 126 may include memory 130 storing computer-readable instructions/code 132 for execution by a processor 134 (e.g., microprocessor) to perform aspects of embodiments of methods and procedures discussed herein.

The various components of the system 100 may be communicatively coupled to each other via communication links 136. In certain embodiments, the communication links 136 may be, or include, a wired communication link (e.g., a serial communication), a wireless communication link such as, for example, a short-range radio link, such as Bluetooth, IEEE 802.11, a proprietary wireless protocol, and/or the like. The term "communication link" may refer to an ability to communicate some type of information in at least one direction between at least two components and may be a persistent communication link, an intermittent communication link, an ad-hoc communication link, and/or the like. The communication links 136 may refer to direct communications between components and/or indirect communications that travel between components via at least one other device (e.g., a repeater, router, hub).

In embodiments, the memory 118 and 130 includes computer-readable storage media in the form of volatile and/or nonvolatile memory and may be removable, non-removable, or a combination thereof. Media examples include Random Access Memory (RAM), Read Only Memory (ROM), Electronically Erasable Programmable Read Only Memory (EEPROM), flash memory, and/or any other non-transitory storage medium that can be used to store information and can be accessed by a computing device. In certain embodiments, the ablation catheter 102 includes memory that stores information unique to the ablation catheter 102 (e.g., catheter ID, manufacturer). This information can be accessed and associated with data collected as part of an ablation procedure (e.g., patient data, ablation parameters).

The computer-executable instructions 120 and 132 may include, for example, computer code, machine-useable instructions, and the like such as, for example, program components capable of being executed by the one or more processors 122 and 134. Some or all of the functionality contemplated herein may be implemented in hardware and/or firmware.

In certain embodiments, the RF generator 114 and the computing device 124 are separate components housed in a single console 138. In certain embodiments, the RF generator 114 and the computing device 124 each include a plurality of controllers and/or processors that are configured to perform aspects of embodiments of methods and procedures discussed herein.

Figure 2:
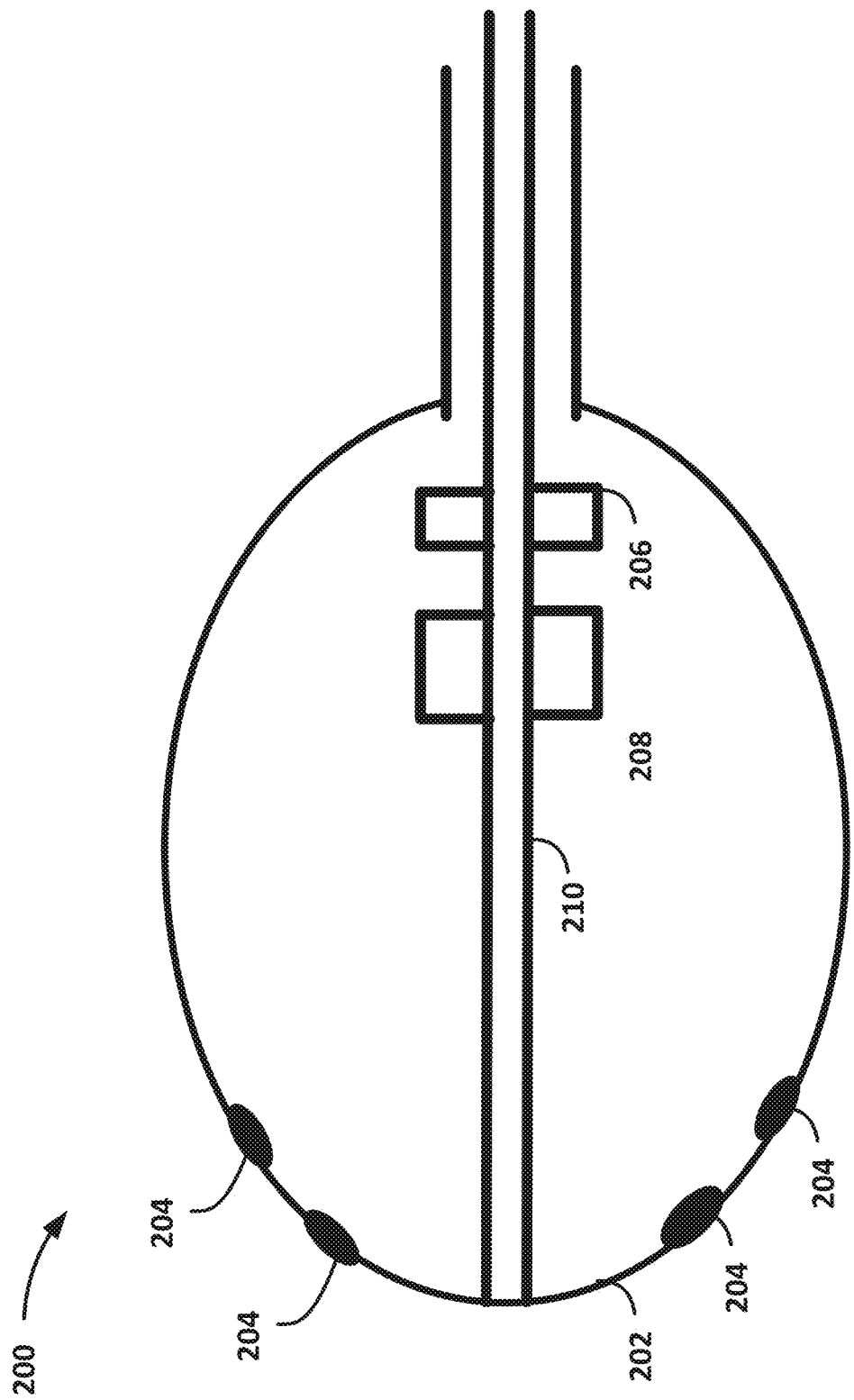
FIG. 2 shows a side, cut-away view of an ablation catheter, in accordance with certain embodiments of the present disclosure.

FIG. 2 shows an ablation catheter 200 that could be used in the system 100. The ablation catheter 200 includes an expandable member 202 and a plurality of energy delivery elements 204 secured to the expandable member 202. The energy delivery elements 204 are configured and positioned to deliver ablative energy to tissue when the expandable member 202 is inflated. Each of the energy delivery elements 204 is individually addressable or can be used with any other energy delivery element 204. The energy delivery elements 204 can operate in a monopolar mode or bipolar mode. Sets of energy delivery elements 204 can be chosen such that the lesion is linear, a spot, a hollow circle, etc. In embodiments utilizing a monopolar mode, the system 100 may include a return pad.

Figure 3:
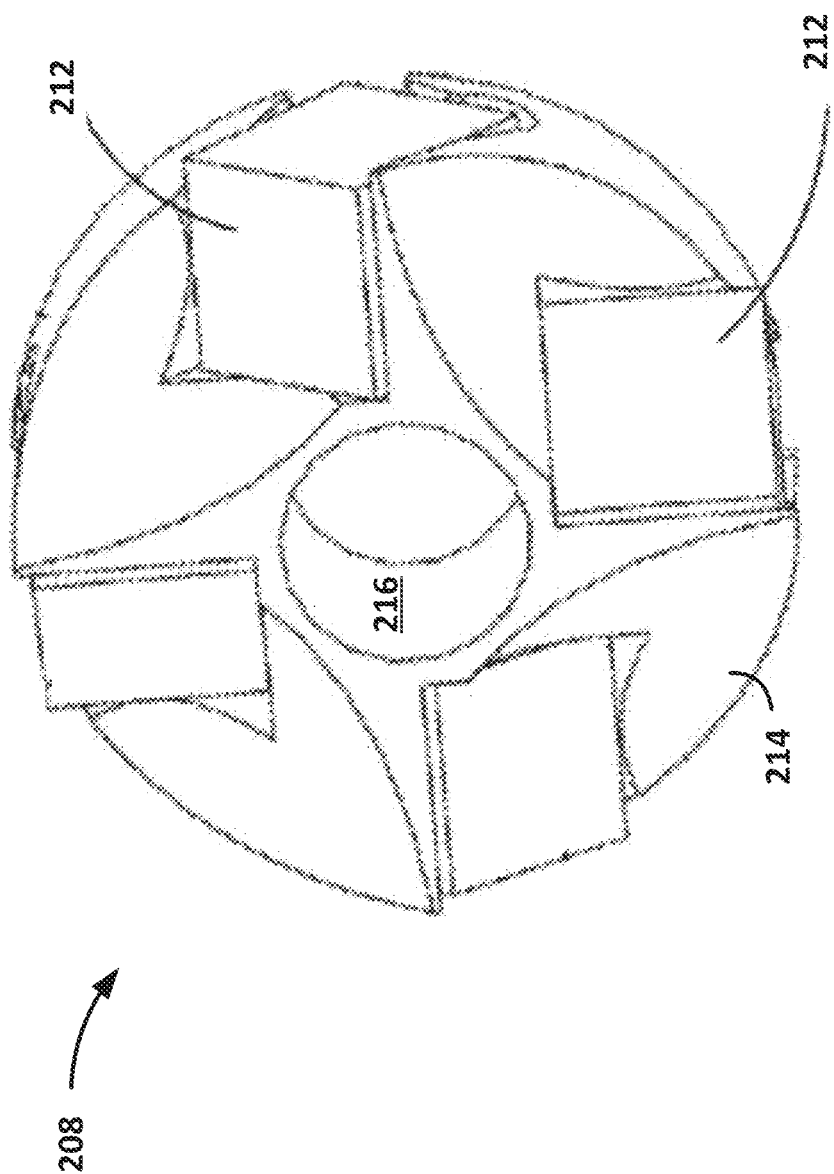
FIGS. 3-11 show various views of a graphical user interface, in accordance with certain embodiments of the present disclosure.

The ablation catheter 200 includes a visualization system 206 including a camera assembly 208 and illumination sources (e.g., light-emitting diodes (LEDs)) disposed on a guide wire shaft 210. As shown in FIG. 3, the camera assembly 208 includes a plurality of cameras 212, which are disposed within a camera hub 214 at an angle relative to a longitudinal axis of the ablation catheter 200. The camera hub 214 is configured to be secured to the guide wire shaft 210 and includes a lumen 216 configured to receive the guide wire shaft 210 therein. The cameras 212 are configured to enable real-time imaging (e.g., video) of an ablation procedure from within the expandable member 202 including visualizing the expandable member 202, the energy delivery elements 204, and cardiac tissue as well as lesion formation during the ablation procedure.

The illumination sources are configured and positioned to provide illumination generally radially outward towards a diffuse reflector. The diffuse reflector thus diffusely reflects light forward toward the cameras' fields of view. The illumination sources thus provide lighting for the cameras 212 to visualize the ablation procedure.

Figure 4:
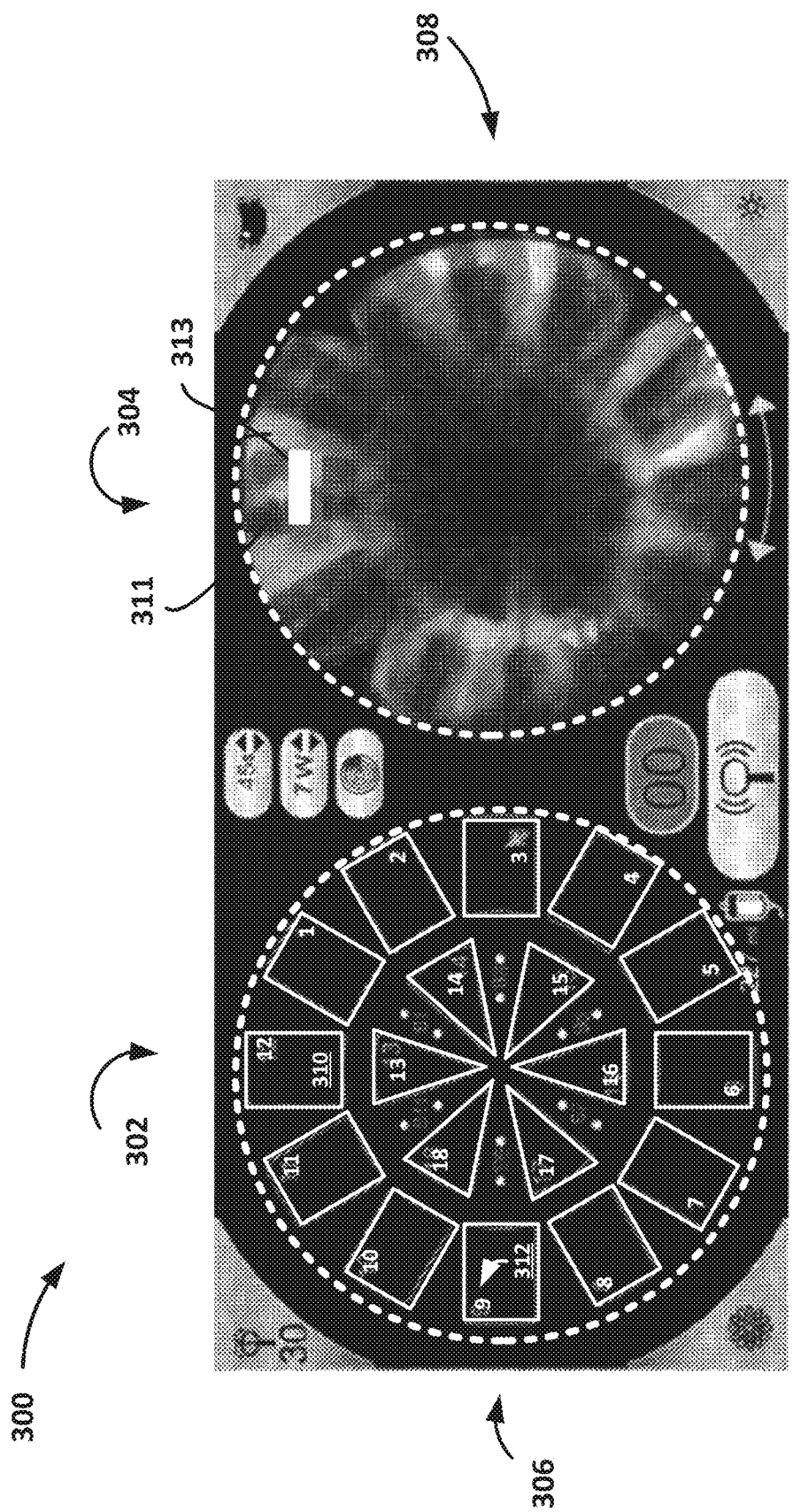

In certain embodiments, some or all of the energy delivery elements 204 of the ablation catheter 200 include an electrode identifier—an example of which, 313, is shown in FIG. 4. The electrode identifier is visually identifiable and helps a user and/or display controllers associate the electrode identifier with one of the energy delivery elements 204. For example, the electrode identifier can be a different color than the rest of the energy delivers element and can form a pattern or shape that is unique to a particular energy delivery element.

As mentioned above, the computing device 124 of the system 100 includes the display controller 126 that is configured to communicate with various components of the system 100 and generate a GUI for displaying via the display 128. FIGS. 4-14 show example GUIs and their various features and views that can be used in the system 100 and displayed via the display 128. Users can interact (e.g., select icons, enter data) with the GUIs using one or more input devices (e.g., mouse, keyboard, touchscreen).

FIG. 4 shows a GUI 300 including a first region 302 and a second region 304. The first region 302 displays a graphical representation 306 of electrodes of an ablation catheter, and the second region 304 displays a real-time video 308 from the ablation catheter. The first region 302 and the second region 304 are shown as being positioned side-byside and being circular-shaped regions. In certain embodiments, the first region 302 and the second region 304 are separate windows within the GUI 300.

The graphical representation 306 includes a separate electrode icon 310 for each of the plurality of electrodes of the ablation catheter. In certain embodiments, each electrode icon 310 is similarly-shaped to an actual shape of a corresponding electrode 311 on the ablation catheter. Each electrode icon 310 can include a unique numerical indicator 312. For example, the ablation catheter being represented by the graphical representation 306 includes twelve electrodes in an outer ring and six electrodes in an inner ring, and each of the electrode icons 310 is assigned an integer (e.g., 1-18).

The displayed real-time video 308 allows for visualization of an ablation procedure, including allowing physicians, etc., to assess the degree of tissue contact and to see the electrodes, tissue, and lesion formation as it occurs along the tissue. The displayed real-time video 308 may include displaying video recorded by one or more cameras. For example, if an ablation catheter (e.g., the ablation catheter 200 of FIGS. 2-4) includes four cameras, the real-time video 308 may display video recorded from each of the four cameras. In such embodiments, the real-time video 308 can display each of the four fields of view from the cameras overlaid with at least one other field of view. This gives the physician, etc., a 360-degree view of the treatment area and allows visualization of contact between the ablation catheter and lesion formation during the ablation procedure. As shown in the displayed real-time video 308 in FIG. 4, an ablation electrode 311 associated with an electrode icon 310 having a numerical indicator 312 of "12" includes an electrode identifier 313, which is seen in the real-time video 308 as a reflective bar or rectangle on the ablation electrode 311. This electrode identifier 313 can be used by a display controller (e.g., the display controller 126 of FIG. 1) to associate the displayed graphical representation 306 with the displayed real-time video 308 and align the real-time video 308 with the graphical representation 306. For example, the electrode icon 310 with the "12" numerical indicator 312 can always be positioned at the top of the graphical representation 306 and the associated ablation electrode 311 in the displayed real-time video 308 can always be positioned at the top.

The GUI 300 includes a number of icons that are associated with and can be used to control or monitor aspects of the ablation catheter and the GUI 300 itself. In certain embodiments described below, the icons can be selected or hovered over to cause the GUI 300 to display additional icons that represent a menu of limited (e.g., four or fewer) pre-selected options, while other icons include buttons that allow selection of more options. Any of the icons described below can be associated with pre-selected options or more user-customizable options.

Figure 5:
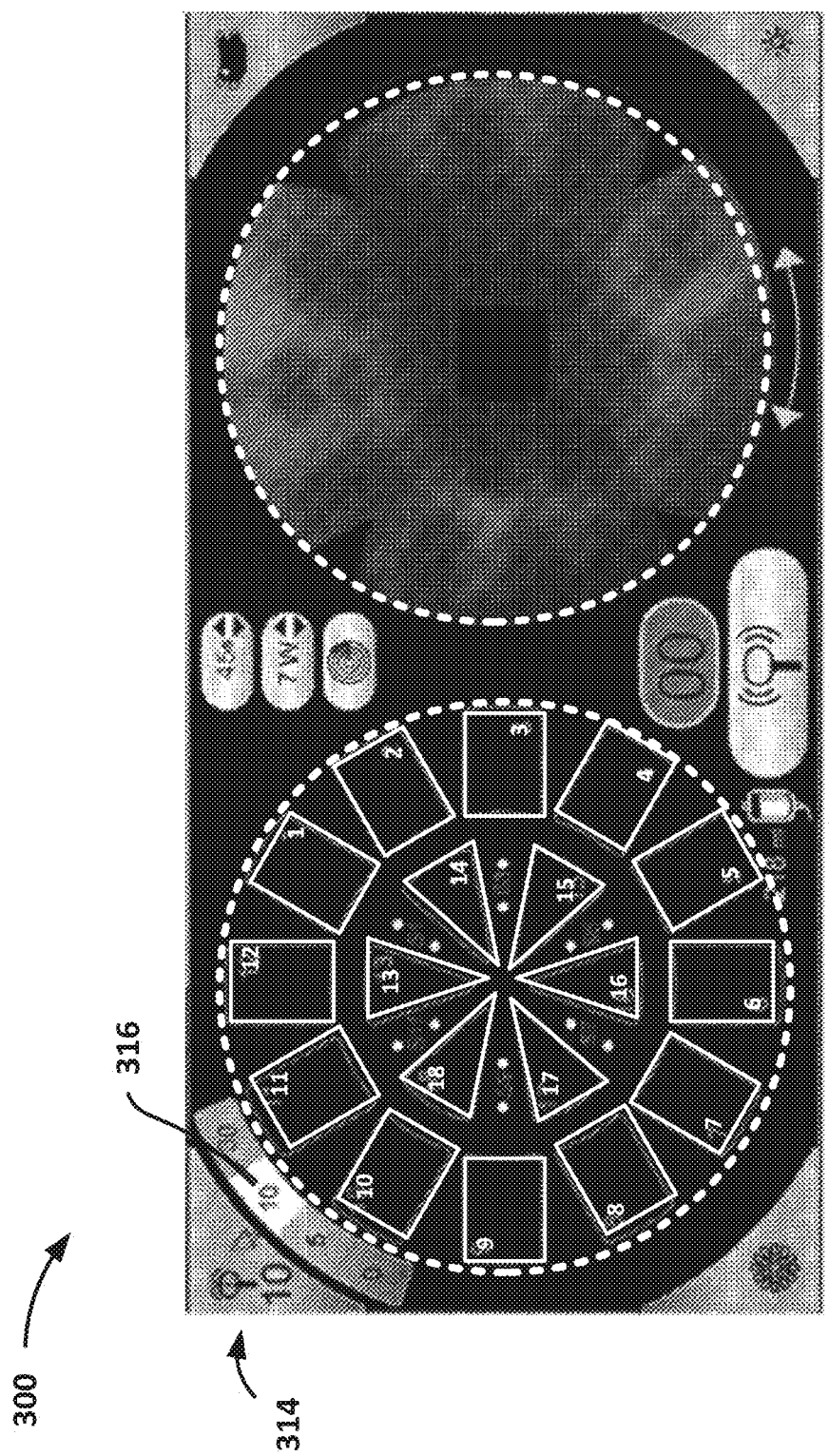

FIG. 5 shows an irrigation icon 314 positioned in an upper-left corner of the GUI 300 and that can be used to control flow rates of irrigation fluid through the ablation catheter. In certain embodiments, the irrigation icon 314 can be selected or hovered over to cause the GUI 300 to display a set of flow rate icons 316 associated with pre-selected flow rates. Once a flow rate is selected, the flow rate icons 316 can disappear from the GUI 300 and the irrigation icon 314 can display the selected flow rate, which is shown as 10 in FIG. 5. Further, once a flow rate is selected, the selected flow rate can be sent to a computing device (e.g., the computing device 124 of FIG. 1) to control an irrigation fluid pump.

Figure 6:
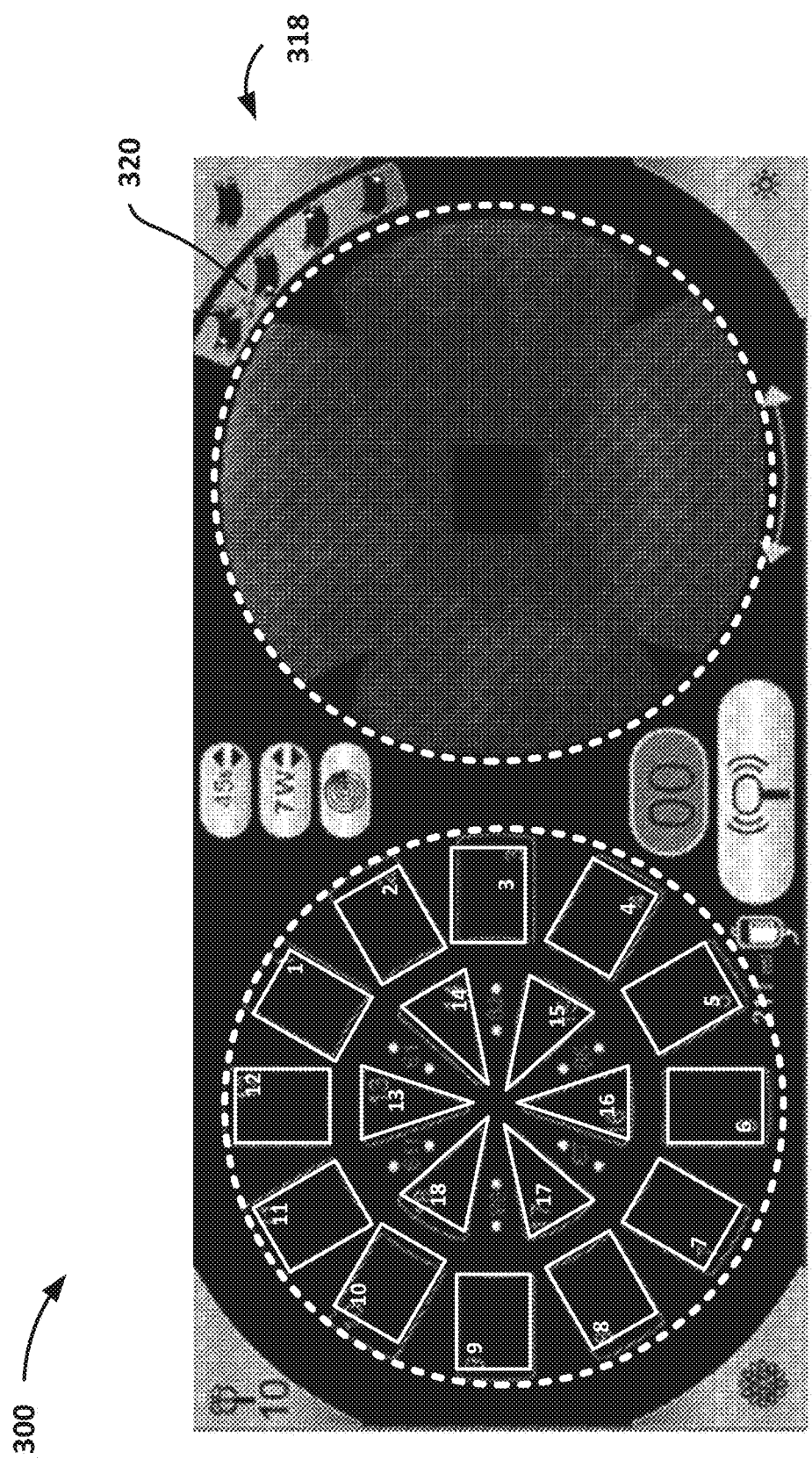

FIG. 6 shows an anatomy icon 318 positioned in an upper-right corner of the GUI 300 and that can be used to identify the pulmonary vein (e.g., right superior, right inferior, left superior, left inferior) to be ablated during the ablation procedure. In certain embodiments, the anatomy icon 318 can be selected or hovered over to cause the GUI 300 to display a set of additional anatomy icons 320 associated with pre-selected anatomical parts. Once an anatomical part is selected, the additional anatomy icons 320 can disappear from the GUI 300 and the anatomy icon 318 can display the selected anatomical part. Further, once an anatomical part is selected, data associated the selected anatomical part can be stored in a memory (e.g., the memory 118 and 130 of FIG. 1).

Figure 7:
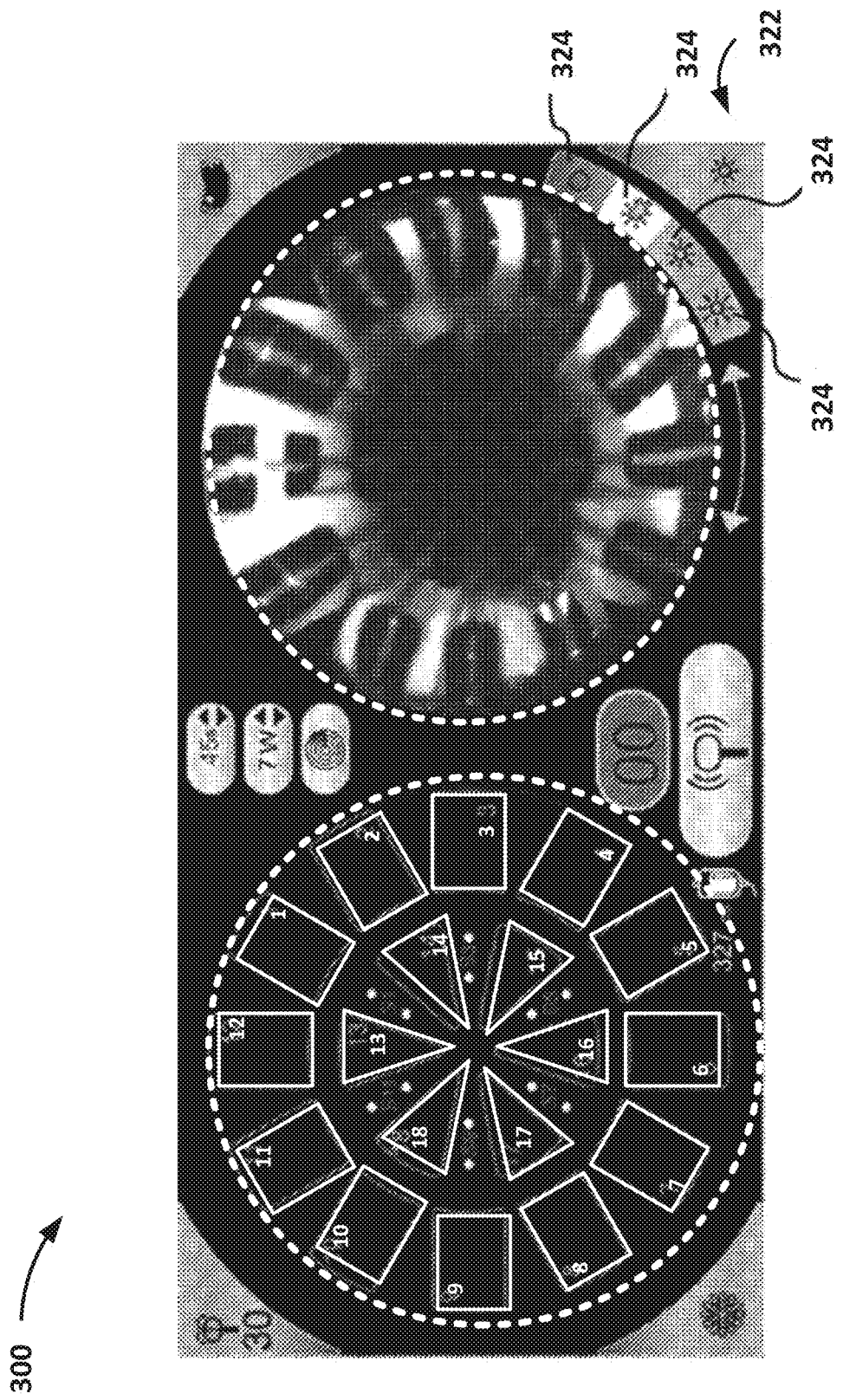

FIG. 7 shows an illumination icon 322 positioned in a lower-right corner of the GUI 300 and that can be used to modify illumination power of illumination sources in the ablation catheter and/or contrast of the real-time video 308 of the GUI 300. In certain embodiments, the illumination icon 322 can be selected or hovered over to cause the GUI 300 to display a set of additional illumination icons 324 associated with pre-selected power and/or contrast levels. Once a power and/or contrast level is selected, the additional illumination icons 324 can disappear from the GUI 300 and the illumination icon 322 can display the selected power and/or contrast level in numerical or graphical form. Further, once a power and/or contrast level is selected, the selected power and/or contrast level can be sent to a computing device (e.g., the computing device 124 of FIG. 1) to control either the illumination power of the illumination sources and/or the contrast of the real-time video displayed in the GUI 300.

Figure 8:
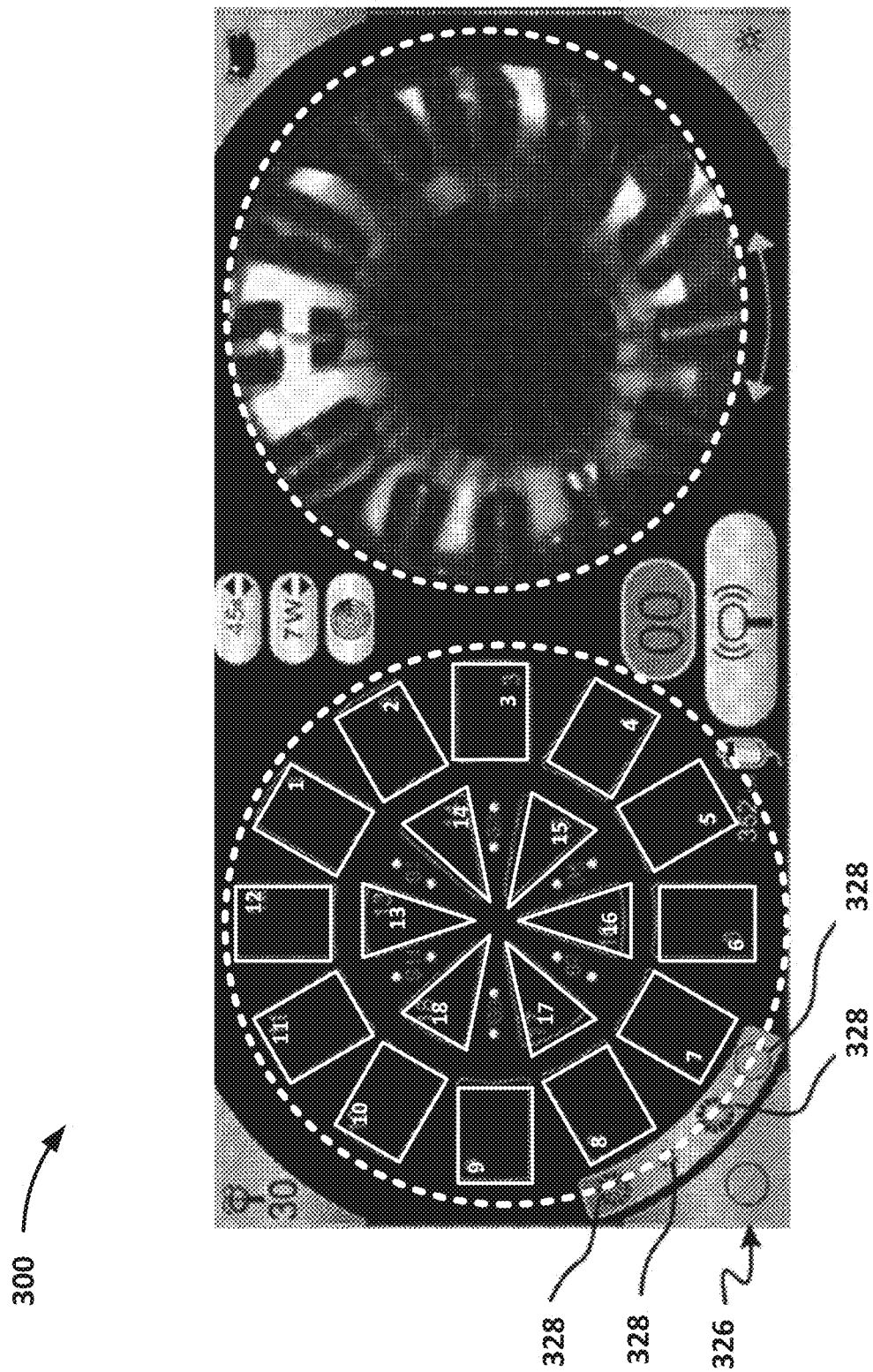

FIG. 8 shows an electrode selection icon 326 positioned in a lower-left corner of the GUI 300 and that can be used to select certain electrode icons 310 of the graphical representation 306. In certain embodiments, the electrode selection icon 326 can be selected or hovered over to cause the GUI 300 to display a set of additional electrode selection icons 328 associated with pre-selected patterns of electrode icons 310 (e.g., inner ring of electrode icons 310, outer ring, all electrode icons 310, none). Once a pattern is selected, the additional electrode selection icons 328 can disappear from the GUI 300 and the electrode selection icon 326 can display the selected pattern graphical form. Further, once a pattern is selected, the selected electrode icons 310 can be highlighted on the GUI 300.

Figure 9:
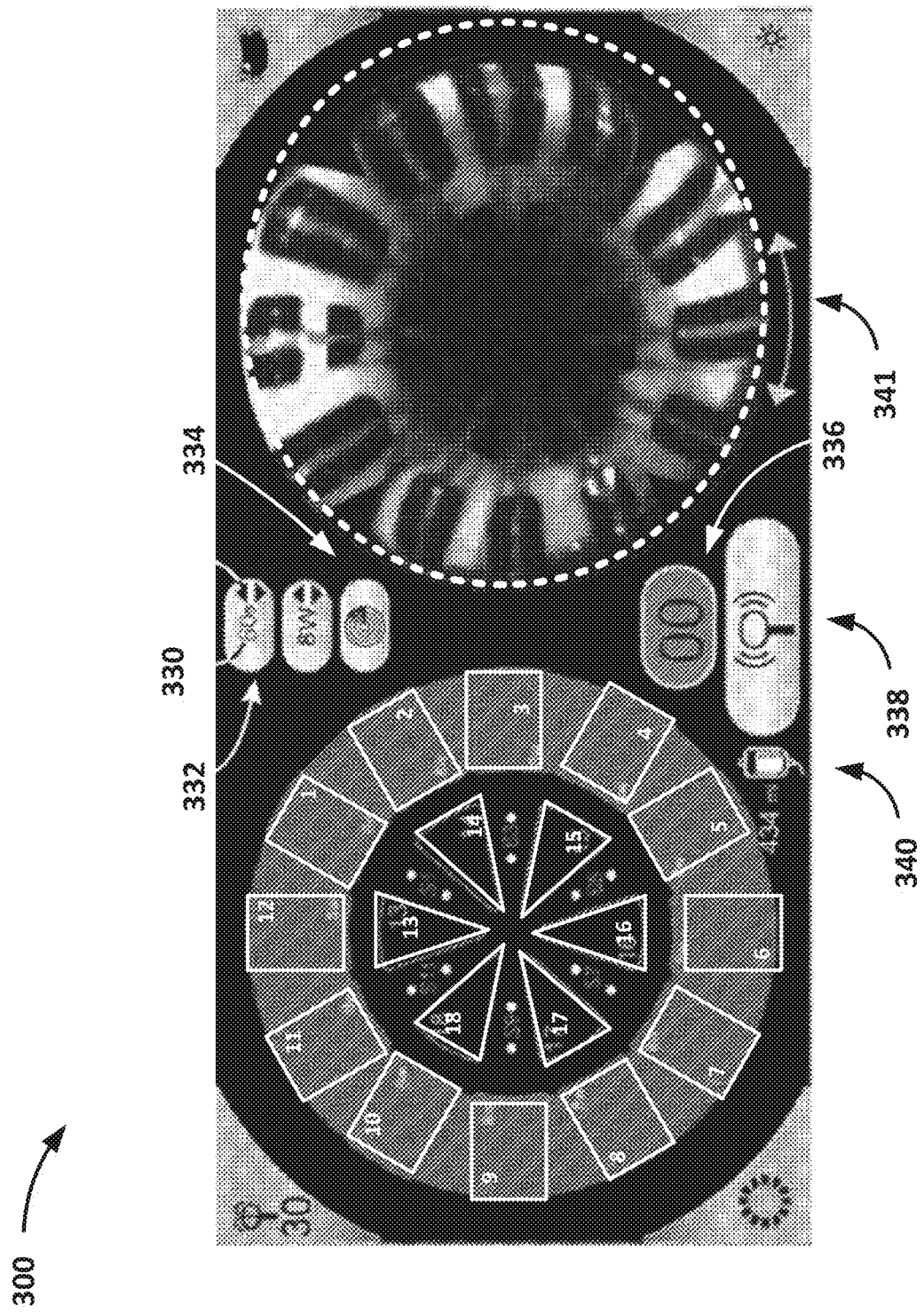

FIG. 9 shows the GUI 300 with an outer ring of electrode icons 310 selected and highlighted. The selected and highlighted electrode icons 310 indicate that, should an ablation procedure begin, only the ablation electrode corresponding to the selected and highlighted electrode icons 310 would be active during the ablation procedure.

FIG. 9 shows the GUI 300 including a procedure timing icon 330, which displays and allows a user to modify, via arrow buttons, the length of time the selected ablation electrodes are to be energized. The GUI 300 also includes a power icon 332, which displays and allows a user to modify, via arrow buttons, a power level (e.g., 7 Watts) at which the selected ablation electrodes will be energized. In certain embodiments, a user can increase or decrease a power level assigned to a given electrode icon 310 by selecting the electrode icon 310 to display a power selection icon, which includes buttons to increase or decrease power. Electrode icons 310 associated with lower or higher power can be shaded or brightened to visually indicate that such electrode icons have a different power.

The GUI 300 also includes an electrode scanning icon 334, which, when selected, initiates a routine that sequentially activates all electrodes to determine whether any electrodes or RF amplifiers are defective. The GUI 300 also includes a timer icon 336, which dynamically displays the length of time of an ablation procedure.

The GUI 300 also includes an ablation activate/deactivate icon 338, which allows the user to initiate or stop energy delivery to the ablation electrodes of the ablation catheter. Once the activate/deactivate icon 338 is pressed to initiate energy delivery, a graphic in the activate/deactivate icon 338 changes (e.g., changes to a stop sign). Further, once the activate/deactivate icon 338 is pressed to initiate energy delivery, a signal is transmitted to an RF generator (e.g., the RF generator 114 of FIG. 1) and/or an RF generator controller (e.g., the RF generator controller 116 of FIG. 1) to start delivering energy to the selected ablation electrodes of the ablation catheter.

FIG. 9 also shows the GUI 300 including a fluid amount icon 340, which indicates the amount of fluid passed through the ablation catheter since entering a patient's body. The GUI 300 can also include a view rotation icon 341, which allows a user to select and rotate both the graphical representation 306 and the real-time video 308.

Figure 10:
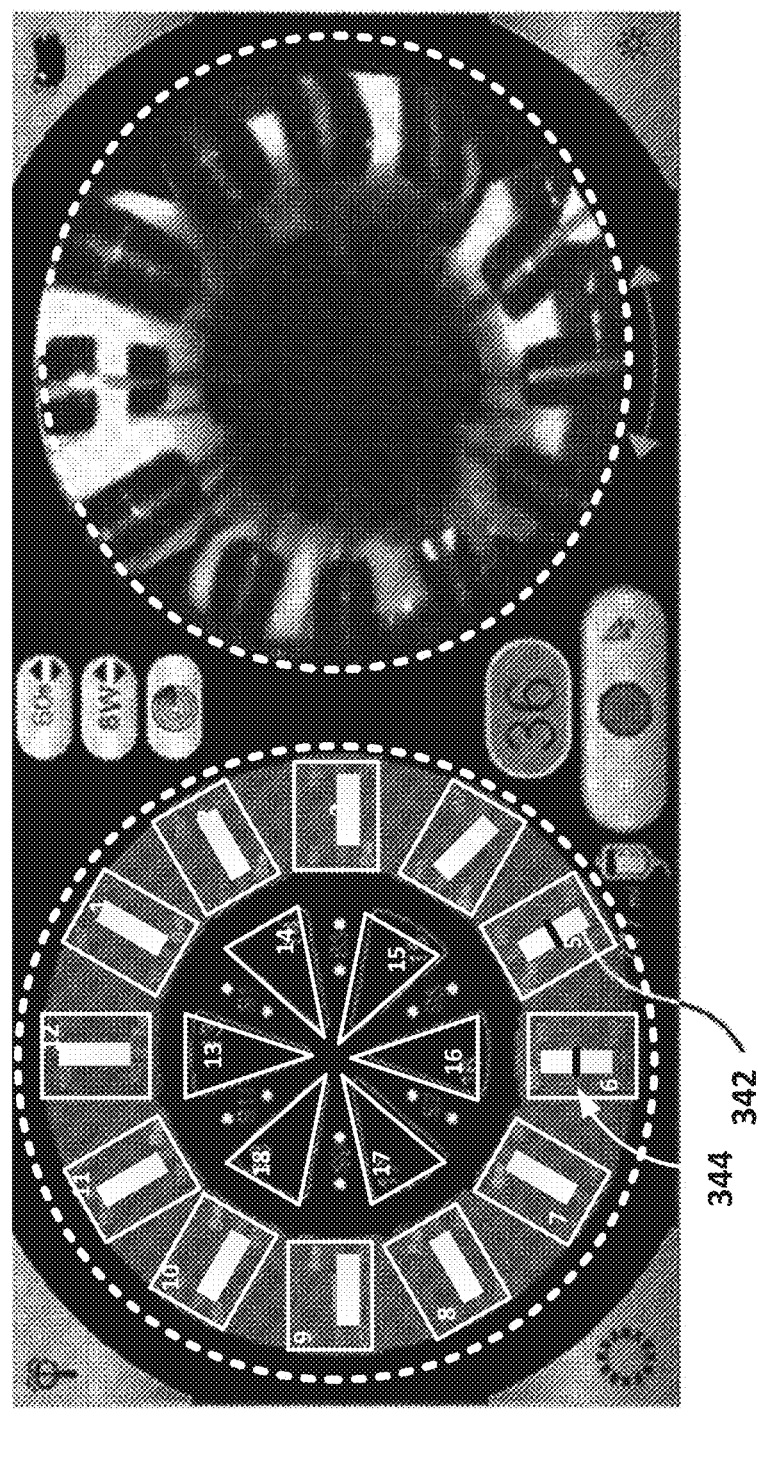
Figure 11:
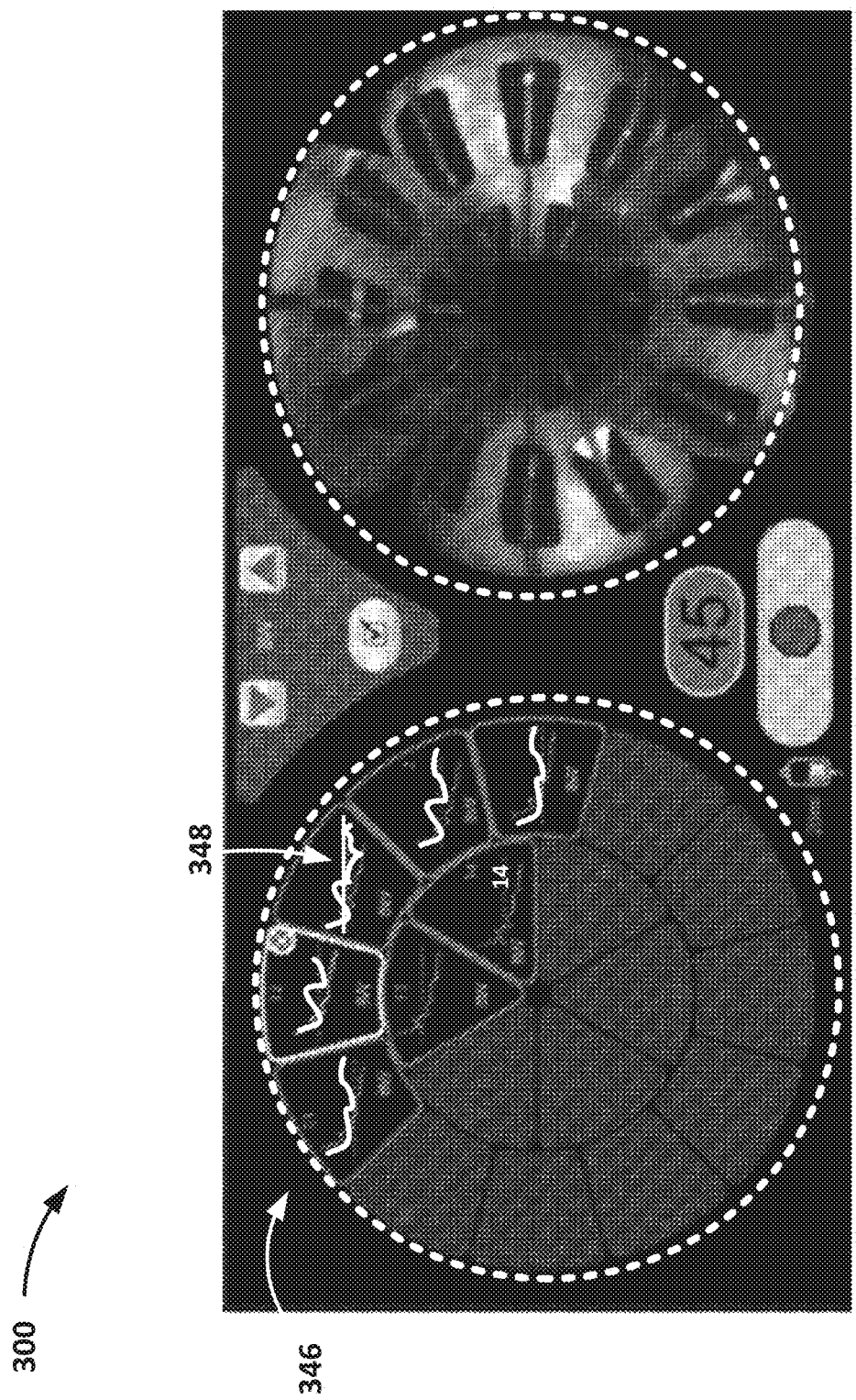

FIGS. 10 and 11 show variations of the GUI 300 while the selected ablation electrodes are energized and ablating tissue. In certain embodiments, some of the icons described above (e.g., certain icons positioned in the corners of the GUI 300) disappear from the GUI 300 such that the GUI 300 has a more simple look and feel.

In both FIGS. 10 and 11, the electrode icons 310 include visual indicators representing electrical impedance of tissue sensed by respective ablation electrodes of the ablation catheter. Electrical impedance of tissue generally decreases as the tissue increases in temperature and lesions form. As such, electrical impedance can indicate whether certain areas of tissue are being (or have been) ablated as desired.

FIG. 10 shows each selected electrode icon 310 (or, if in a bipolar mode, each selected source) including an impedance bar 342. Each impedance bar 342 can represent a range of impedance and can include a real-time impedance value indicator 344 that indicates the real-time sensed impedance within the range for each electrode icon 310. In certain embodiments, the portion of the impedance bar 342 representative of impedance higher than the real-time sensed electrical impedance can be displayed in a different color to help visualize progress of lesion formation. In certain embodiments, the impedance bar 342 can include an alarm indicator set to indicate a level of electrical impedance indicative of desirable lesion formation. In embodiments, the GUI 300 can display an alert/alarm visual (e.g., flashing electrode icon 310, different colored electrode icon 310) to indicate the alarm threshold has been breached.

FIG. 11 shows each selected electrode icon 310 (or, if in a bipolar mode, each selected source) including an impedance plot 346. Each impedance plot 346 can be created in real-time as the level of sensed electrical impedance changes. In certain embodiments, the impedance plot 346 can include an alarm indicator 348 (e.g., line) set to indicate a level of electrical impedance indicative of desirable lesion formation. In embodiments, the GUI 300 can display an alert/alarm visual (e.g., flashing electrode icon 310, different colored electrode icon 310) to indicate the alarm threshold has been breached. In the above-described embodiments of FIGS. 10 and 11, signals indicative of the electrical impedance sensed by respective ablation electrodes are transmitted to a computing device (e.g., the computing device 124 of FIG. 1) for processing and generating features of the impedance bar 342 and/or the impedance plot 346. In certain embodiments, multiple lines can be used to represent the percentage change of tissue impedance. Effective lesions can sometimes be identified by their percentage change in impedance.

Figure 12:
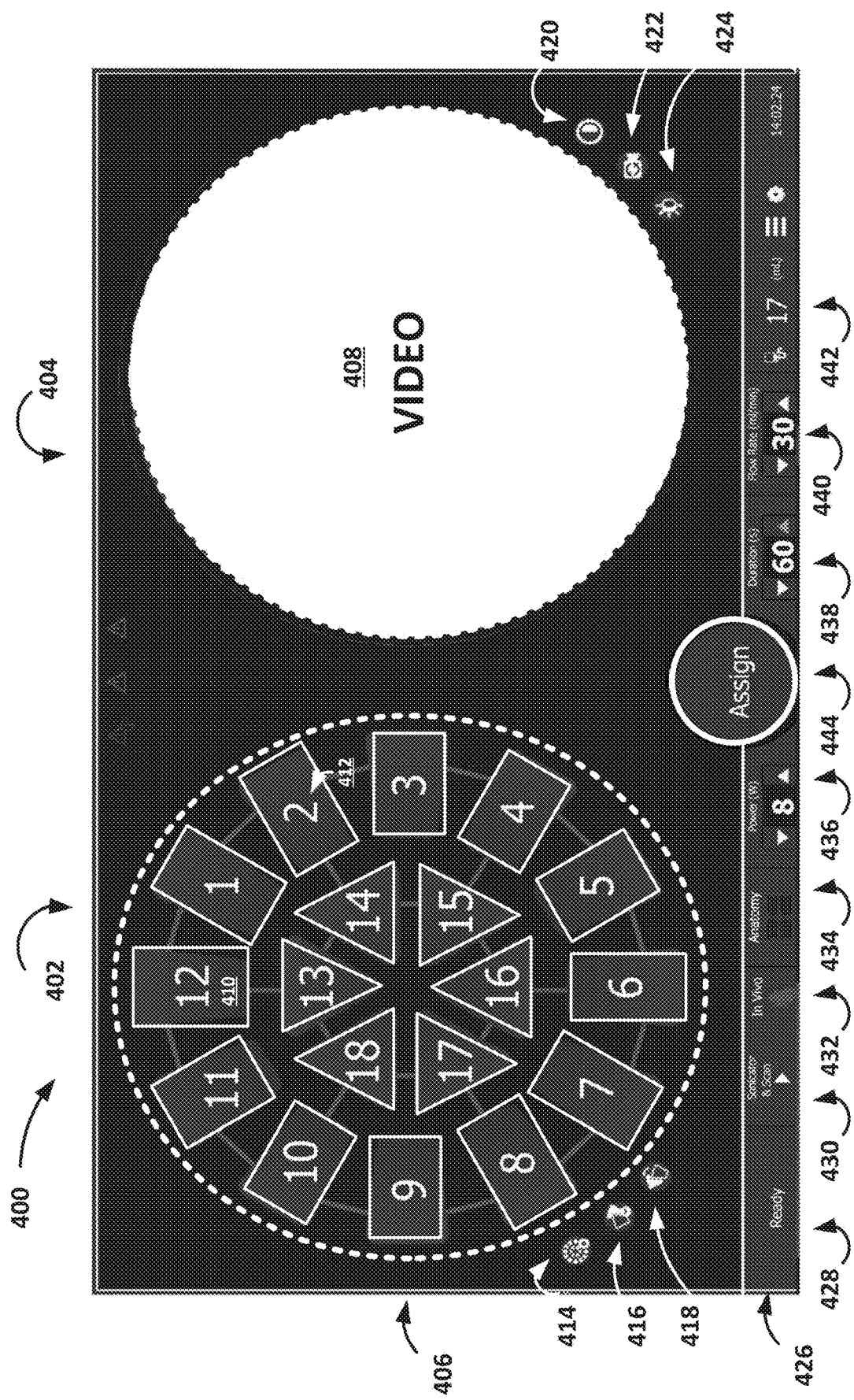
FIGS. 12-14 show various views of another graphical user interface, in accordance with certain embodiments of the present disclosure.
Figure 13:
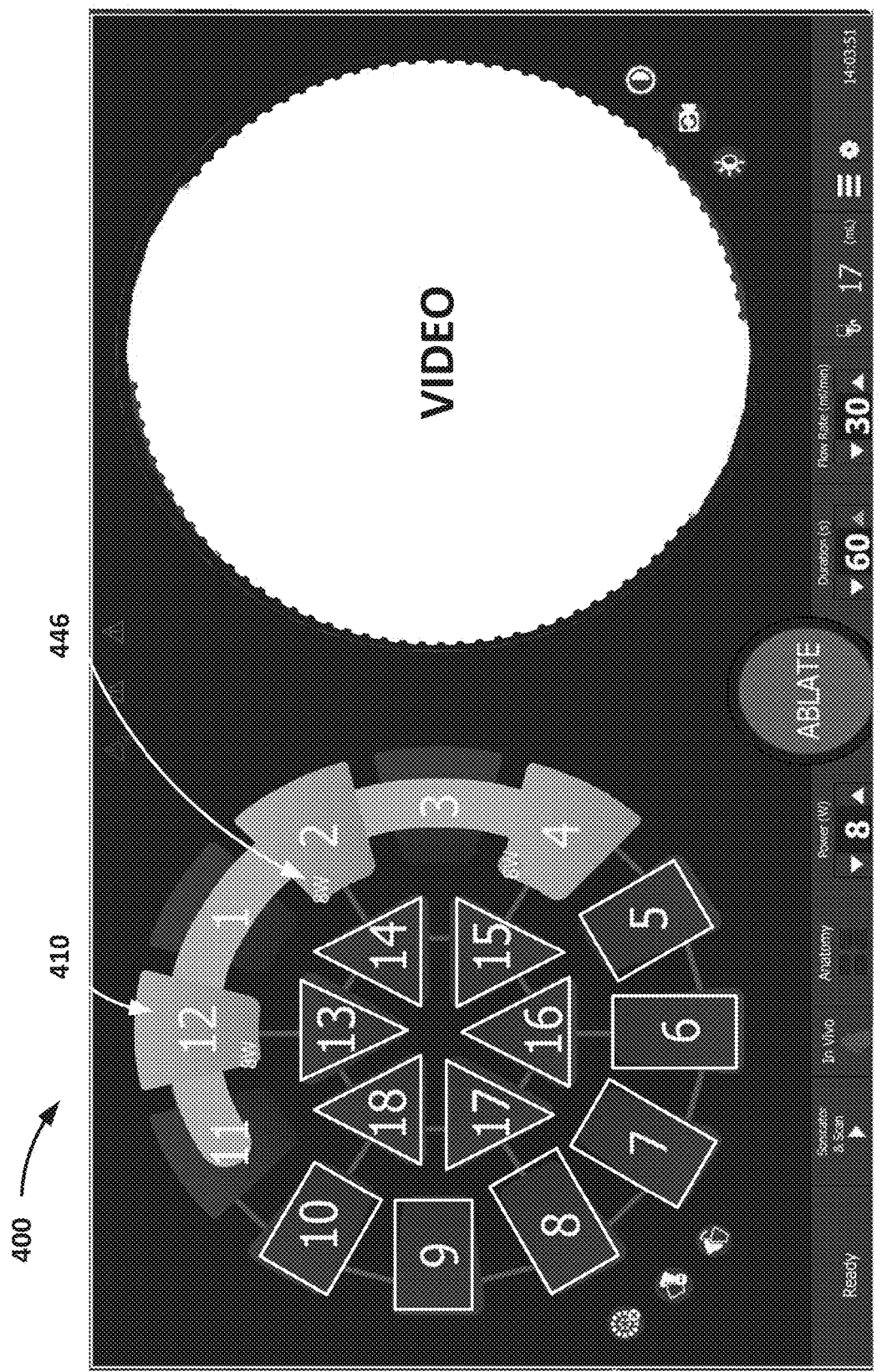
Figure 14:
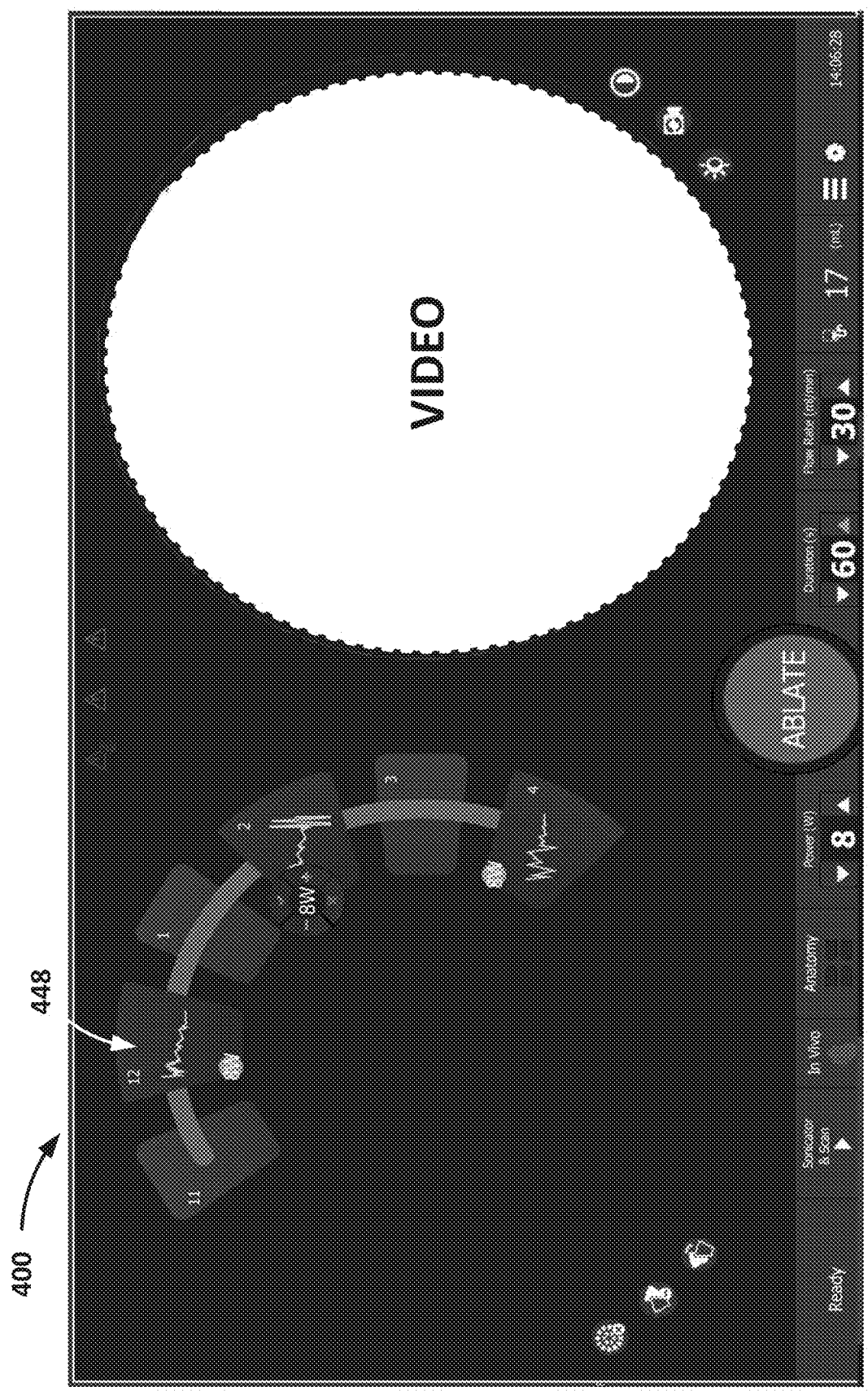

FIGS. 12-14 show a GUI 400 including a first region 402 and a second region 404. The first region 402 displays a graphical representation 406 of electrodes of an ablation catheter, and the second region 404 displays a real-time video 408 from the ablation catheter. The first region 402 and the second region 404 are shown as being positioned side-by-side and being circular-shaped regions.

The graphical representation 406 includes a separate electrode icon 410 for each of the plurality of electrodes of the ablation catheter. In certain embodiments, each electrode icon 410 is similarly-shaped to an actual shape of a corresponding electrode on the ablation catheter. Each electrode icon 410 can include a unique numerical indicator 412. For example, in the embodiment shown in FIGS. 12-14, the ablation catheter being represented by the graphical representation 406 includes twelve electrodes in an outer ring and six electrodes in an inner ring, and each of the electrode icons 410 is assigned an integer (e.g., 1-18).

The displayed real-time video 408 allows for visualization of an ablation procedure. The displayed real-time video 408 may include displaying video recorded by one or more cameras. For example, if an ablation catheter (e.g., the ablation catheter 200 of FIG. 2) includes four cameras, the real-time video 408 may display video recorded from each of the four cameras. In such embodiments, the real-time video 408 can display each of the four fields of view from the cameras overlaid with at least one other field of view as shown in FIGS. 12-14.

Like the GUI 300 of FIGS. 4-11, the GUI 400 includes a number of icons that are associated with and can be used to control or monitor aspects of the ablation catheter and the GUI 400 itself.

FIG. 12 shows the GUI 400 including icons relating to the graphical representation 406 positioned in or near the first region 402 next to the graphical representation 406. For example, the GUI 400 includes three icons (i.e., an electrode selection icon 414, an electrode refresh icon 416, and a source-sink reverse icon 418) positioned next to the graphical representation 406 and that affect features of the graphical representation 406. The electrode selection icon 414 can be used to select a pattern from a pre-determined menu of patterns of electrode icon selections. Once a pattern is selected, the selected electrode icons 410 can be highlighted on the GUI 400. The electrode refresh icon 416 can be used to unselect any electrode icon 410 that has been selected. The source-sink reverse icon 418 can be used in a bipolar mode to reverse which electrode icons 410 correspond to a sink and which electrode icons 410 correspond to a source.

FIG. 12 shows the GUI 400 including icons relating to the real-time video 408 positioned in or near the second region 404 next to the real-time video 408. For example, the GUI 400 includes three icons (i.e., a contrast icon 420, a luminosity icon 422, and a video refresh icon 424) positioned next to the real-time video 408 and that affect features of the real-time video 408. The contrast icon 420 can be used to increase or decrease contrast of the real-time video 408. The luminosity icon 422 can be used to modify illumination power of illumination sources in the ablation catheter. The video refresh icon 424 can be used to refresh the video feed and/or a display controller if the real-time video 408 encounters problems.

The GUI 400 includes a ribbon 426 with various icons relating to the ablation catheter and/or the GUI 400 itself. The ribbon 426 includes a status icon 428 indicating the system's status and a sonic/scan icon 430, which initiates a routine for initiating an ultrasonic source and for scanning the electrodes on the ablation catheter to identify potentially faulty electrodes. For example, the ablation catheter may be placed in a bath coupled to an ultrasonic source, and once the sonic/scan icon 430 is selected, the routine can turn on the ultrasonic source for a predetermined period of time to remove air bubbles stuck to the ablation catheter before a treatment procedure. After expiration of the predetermined period of time, the routine can sequentially activate all electrodes to determine whether any electrodes or RF amplifiers are defective. If the ultrasonic source is not connected, the sonic/scan icon 430 will just initiate the scanning portion of the routine.

The ribbon 426 also includes an in vivo icon 432, which can be selected to indicate that the ablation catheter has been placed within a patient; an anatomy icon 434, which can be used to identify the pulmonary vein to be treated; a power icon 436, which displays and allows a user to modify, via arrow buttons, a power level at which the selected ablation electrodes will be energized; a procedure timing icon 438, which displays and allows a user to modify, via arrow buttons, the length of time the selected ablation electrodes are to be energized; an irrigation flow rate icon 440, which can be used to control flow rates of irrigation fluid through the ablation catheter; and a fluid volume icon 442, which indicates the amount of fluid passed through the ablation catheter since the in vivo icon 432 was selected.

The GUI 400 also includes an ablation activate/deactivate icon 444, which allows the user to initiate or stop energy delivery to the ablation electrodes of the ablation catheter. In FIG. 12, the ablation activate/deactivate icon 444 includes text stating "Assign." When selected, a computing device assigns the selected electrode icons 410 as being a source or a sink. FIG. 13 shows a view of the GUI 400 after selecting the "Assign" feature. For example, electrode icons 410 numbered "11", "12", and "1" through "4" were selected before selecting the "Assign" feature and are highlighted in FIG. 13. Electrode icons 410 numbered "12", "2", and "4" are fully highlighted and include a power icon 446. This indicates that electrodes 12, 2, and 4 have been assigned as source electrodes and electrodes 11, 1, and 3 have been assigned as sink electrodes.

In FIG. 13, the ablation activate/deactivate icon 444 includes text stating "ABLATE." When selected, the activate/deactivate icon 444 initiates energy delivery by transmitting a signal to an RF generator (e.g., the RF generator 114 of FIG. 1) and/or an RF generator controller (e.g., the RF generator controller 116 of FIG. 1) to start delivering energy to ablation electrodes on the ablation catheter associated with the selected electrode icons 410 assigned to be a source electrode.

FIG. 14 shows the GUI 400 while the selected ablation electrodes are energized and ablating tissue. FIG. 14 shows each selected electrode icon 410 (or, if in a bipolar mode, each selected source) including an impedance plot 448. Each impedance plot 448 can be created in real-time as the sensed electrical impedance changes. In certain embodiments, multiple lines can be used to represent the percentage change of tissue impedance. Effective lesions can sometimes be identified by their percentage change in impedance. In certain embodiments, the impedance plot 448 can include an alarm indicator (e.g., line) set to indicate a level of electrical impedance indicative of desirable lesion formation. In embodiments, the GUI 400 can display an alert/alarm visual (e.g., flashing electrode icon 410, different colored electrode icon 410) to indicate the alarm threshold has been breached. Signals indicative of the electrical impedance sensed by respective ablation electrodes are transmitted to a computing device (e.g., the computing device 124 of FIG. 1) for processing and generating features of the impedance plot 448.

As shown in FIGS. 13 and 14, each of the source electrode icons 410 includes a power icon 446, which displays the current power assigned to the corresponding ablation electrode and which can be selected to display a power selector icon. The power selector icon includes icons that can be used to increase and decrease power assigned to the individual corresponding ablation electrode. The amount of power for each electrode can be modified in real time.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An ablation system comprising:
   a radiofrequency (RF) generator configured to generate RF energy; and
   one or more controllers in communication with the RF generator and configured to:
      generate a real-time video from an ablation catheter for displaying via a graphical user interface (GUI),
      generate a graphical representation including electrode icons corresponding to a plurality of electrodes of the ablation catheter for displaying via the GUI,
      wherein the plurality of electrodes are configured to sense electrical impedance,
      generate electrical impedance plots based on sensed electrical impedance, the electrical impedance plots to be displayed within at least some of the electrode icons on the GUI,
      wherein each of the electrical impedance plots comprises a time-variation sequence of electrical impedances,
      receive input, via the graphical representation, selecting at least some of the electrode icons, and
      cause the RF generator to transmit RF energy to the plurality of electrodes of the ablation catheter corresponding to the selected electrode icons.

2. The ablation system of claim 1, further comprising:
   the ablation catheter in communication with the RF generator and including an expandable member carrying the plurality of electrodes.

3. The ablation system of claim 2, wherein the ablation catheter includes cameras for generating video for the real-time video of the GUI.

4. The ablation system of claim 2, wherein the ablation catheter includes an illumination source, wherein the GUI includes an illumination icon for selecting power to the illumination source, wherein the one or more controllers is configured to:
   modify power to the illumination source based on the selected power from the illumination icon.

5. The ablation system of claim 1, further comprising:
   a display in communication with the one or more controllers and configured to display the GUI.

6. The ablation system of claim 1, further comprising:
a computer readable storage medium having program code stored thereon for execution by the one or more controllers to generate the GUI.

7. The ablation system of claim 1, wherein the one or more controllers is configured to:
generate electrical impedance plots to be displayed within at least some of the electrode icons in the GUI.

8. The ablation system of claim 1, wherein the electrode icons of the graphical representation are selectable via the GUI, wherein the one or more controllers is configured to:
assign the selected electrode icons as either a source electrode or a sink electrode.

9. The ablation system of claim 1, wherein the RF generator and the one or more controllers are housed in a single console.

\* \* \* \* \*